(12) United States Patent
D'Amico et al.

(10) Patent No.: US 6,368,598 B1
(45) Date of Patent: Apr. 9, 2002

(54) DRUG COMPLEX FOR TREATMENT OF METASTATIC PROSTATE CANCER

(75) Inventors: Anthony V. D'Amico, Westav; Glenn J. Bubley, Walpole; David J. Jebaratnam, Lexington; James S. Weinberg, Dover, all of MA (US)

(73) Assignee: JCRT Radiation Oncology Support Services, Inc., Boston, MA (US)

( * ) Notice: Subject to any disclaimer, the term of this patent is extended or adjusted under 35 U.S.C. 154(b) by 0 days.

(21) Appl. No.: 09/110,822

(22) Filed: Jul. 6, 1998

Related U.S. Application Data (63) Continuation-in-part of application No. 09/003,838, filed on Jan. 7, 1998, now abandoned, which is a continuation of application No. 08/713,114, filed on Sep. 16, 1996, now abandoned.

(51) Int. Cl.$^7$ ............................................. A61K 39/395
(52) U.S. Cl. ............................... 424/181.1; 424/179.1; 424/182.1; 514/12
(58) Field of Search .......................... 424/181.1, 182.1, 424/179.1; 514/12

(56) References Cited

U.S. PATENT DOCUMENTS

| | | | |
|---|---|---|---|
| 5,208,020 A | 5/1993 | Chari et al. | 424/85.91 |
| 5,416,064 A | 5/1995 | Chari et al. | 514/229.5 |
| 5,475,092 A | 12/1995 | Chari et al. | 530/391.7 |
| 5,585,499 A | 12/1996 | Chari et al. | 548/420 |
| 5,599,686 A | 2/1997 | DeFeo-Jones et al. | 435/23 |
| 5,846,545 A | 12/1998 | Chari et al. | 424/195.11 |
| 5,866,679 A | 2/1999 | DeFeo-Jones et al. | 530/322 |
| 6,214,345 B1 | 4/2001 | Firestone et al. | 424/178.1 |

FOREIGN PATENT DOCUMENTS

| | | |
|---|---|---|
| EP | 0 745 390 A2 | 12/1996 |
| WO | WO 97/12624 | 4/1997 |

OTHER PUBLICATIONS

Denmeade, S.R., et al., "Enzymatic Activation of a Doxorubicin–Peptide Prodrug by Prostate–Specific Antigen," *Cancer Research*, 58:2537–2540 (1998).

Denmeade, S.R. and Isaacs, J.T., "Enzymatic Activation of Prodrugs by Prostate–Specific Antigen: Targeted Therapy for Metastatic Prostate Cancer," *The Cancer Journal from Scientific American*, 4(1) :S15–S21 (1998).

Denmeade, S.R., et al., "Role of Programmed (Apoptotic) Cell Death During the Progression and Therapy for Prostate Cancer," *The Prostate* 28251–265 (1996).

Oesterling, Joseph E., "Prostate Specific Antigen: A Critical Assessment of the Most Useful Tumor Marker for Adenocarcinoma of the Prostate," *The Journal of Urology* 145:907–923 (1991).

Kreis, Willi, "Current Chemotherapy and Future Directions in Research for the Treatment of Advanced Hormone–Refractory Prostate Cancer," *Cancer Investigation*, 13(3) : 296–312 (1995).

Christensson, A., et al., "Enzymatic activity of prostate–specific antigen and its reactions with extracellular serine proteinase inhibitors," *Eur. J. Biochem.* 194:755–765 (1990).

Watt, K.W.K. et al., "Human prostate–specific antigen: Structural and functional similarity with serine proteases," *Proc. Natl. Acad. Sci. USA*, 83:3166–3170 (1986).

Lilja, H., et al., "Prostate–Specific Antigen in Human Serum Occurs Predominantly in Complex with $\alpha_1$–Antichymotrypsin," *Clin. Chem.* 37:1618–1625 (1991).

Lilja, H., et al., "Semenogelin, the Predominant Protein in Human Semen," *J. Biol. Chem.* 264:1894–1900 (1989).

Christensen, S.B., et al., "Derivatives of thapsigargin as probes of its binding site on endoplasmic reticulum $Ca^{2+}$ ATPase," *FEBS* 335(3) :345–348 (1993).

Hwang, D–R, et al., "N–3–[$^{18}$F] Fluoropropylputrescine as Potential PET Imaging Agent for Prostate and Prostate Derived Tumors," *J. Nucl. Med.* 30:1205–1210 (1989).

Thastrup, O., et al., "Thapsigargin, a tumor promoter, discharges intracellular $Ca^{2+}$ stores by specific inhibition of the endoplasmic reticulum $Ca^{2+}$–ATPase," *Proc. Nat. Acad. Sci. USA* 87:2466–2470 (1990).

Nogusa, H., et al., "Synthesis of Carboxymethypullulan–Peptide–Doxorubicin Conjugates and Their Properties," *Chem. Pharm. Bull.* 43(11) :1931–1936 (1995).

Israel, M., et al., "Amelioration of adriamycin toxicity through modification of drug–DNA binding properties," *Cancer Treatment Reviews* 14:163–167 (1987).

*Primary Examiner*—Geetha P. Bansal
(74) *Attorney, Agent, or Firm*—Hamilton, Brook, Smith & Reynolds, P.C.

(57) ABSTRACT

A drug complex for delivery of a drug or other agent to a target cell, comprising a targeting carrier molecule which is selectively distributed to a specific cell type or tissue containing the specific cell type; a linker which is acted upon by a molecule which is present at an effective concentration in the environs of the specific cell type; and a drug or an agent to be delivered to the specific cell type. In particular, a drug complex for delivering a cytotoxic drug to prostate cancer cells, comprising a targeting carrier molecule which is selectively delivered to prostate tissue, bone or both; a peptide which is a substrate for prostate specific antigen; and a cytotoxic drug which is toxic to androgen independent prostate cancer cells.

9 Claims, 4 Drawing Sheets

DRUG COMPLEX FOR TREATMENT OF METASTATIC PROSTATE CANCER

RELATED APPLICATION

This application is a continuation-in-part of Ser. No. 09/003,838 filed Jan. 7, 1998 (now abandoned), which is a continuation of Ser. No. 08/713,114 filed Sep. 16, 1996, now abandoned, the teachings of which are incorporated herein in their entirety.

BACKGROUND OF THE INVENTION

Prostate cancer is the second most common malignancy in men and is the third most common cause of cancer death in men older than age 55. *Harrison's Principles of Internal Medicine*, Eds. J. D. Wilson et al., 11th Edition, pp. 1630–1633, McGraw Hill, New York, 1991. New methods of identifying and treating prostate cancer early are extremely important in saving the lives of those afflicted. Presently, only a limited number of treatments are available for treatment of prostate cancer. These treatments include surgery, radiation therapy, and androgen deprivation.

There is a need for additional methods of treatment of prostate cancer.

SUMMARY OF THE INVENTION

The present invention relates to a method of delivering a drug to a specific cell type, such as a cancer cell, in an individual by means of a drug complex which comprises three components and is also the subject of the present invention. The three components of the drug complex include the following: a targeting carrier molecule; a linker which is acted upon by a molecule present at an effective concentration in the environs of the specific cell (referred to as a target cell); and a drug (or agent) to be delivered to the specific cell type. The targeting carrier molecule is one which is delivered specifically to (has a biodistribution which favors) a specific cell type, or tissue containing the specific cell type, to which the drug is to be delivered. The linker can be any type of molecule such as a peptide, provided that it is a substrate for a molecule, such as an enzyme (e.g., a protease), which is found in the environs of the target cell to which the drug is to be delivered and is present in sufficient quantities at the site(s) of the target cell to act upon the linker and release the drug or agent to be delivered, such as by cleaving the linker. The linker can comprise more than one type of molecule. For example, the linker can comprise a component which is a substrate for a molecule which acts upon it and releases the drug to be delivered and an additional component(s), such as a molecule which acts as a good leaving group; additional amino acid residues or other molecule, such as one which acts as a spacer between the targeting carrier molecule and the drug to be delivered. The drug or agent to be delivered can be any therapeutically or diagnostically useful drug or agent, such as a cytotoxic drug or an imaging agent. It remains essentially functionally inactive while it is a component of the drug complex; upon release at the site(s) of the target cells, the drug is functionally active (exerts or displays its therapeutic or diagnostic function(s)). In one embodiment, the linker comprises a substrate for a molecule as described previously, and one or more other additional components, such as chemical molecules, e.g. para-amino benzoic acid (pABA) and para-aminobenzyloxycarbonyl (pABOC), which are good leaving groups. Optionally, there can be amino acid residues in addition to those acted upon by the enzyme or other molecule. Such amino acid residues can be at either or both ends (amino and/or carboxy terminus) of the amino acid residues acted upon. In one embodiment, additional amino acid residue (or residues) is/are included between the carboxy terminal amino acid of the substrate and the drug or agent to be delivered. Cleavage of the substrate results in a product in which an amino acid residue(s) is attached to the drug or agent delivered to the target cell. Such amino acid residues can be, for example, one or more amino acid residues of the substrate (e.g., if the enzyme cleaves at an internal amino acid residue in the substrate), one or more amino acid residues which are not substrate amino acid residues (e.g., if the enzyme cleaves between the carboxyl terminal amino acid residue of the substrate and the amino terminal amino acid residue of additional amino acids) or both. The additional amino acid residue(s) between the substrate carboxyl terminal amino acid residue and the drug or agent to be delivered to the target cell can be linked to the drug or agent in such a manner (e.g., through an amide bond, disulfide bond or ester bond) that cellular enzymes act upon them; resulting in release of the amino acid residue(s) attached to the drug or agent when it enters the cell. The drug or agent to be delivered can be any therapeutically or diagnostically useful drug or agent, such as a cytotoxic drug or an imaging agent.

The present invention also relates to a method of delivering a drug to a specific cell type by means of the drug complex described herein. In the method, the drug complex is administered to an individual in need of therapy or in whom a diagnostic procedure or assessment is to be conducted.

In one embodiment, the present invention is a method of killing prostate cancer cells, including metastatic prostate cancer cells or androgen independent prostate cancer cells, in a man with prostate cancer. The method is particularly effective because it makes use of a drug complex whose components provide the basis for localization to and killing prostate cancer cells, particularly androgen-independent cancer cells. The method of killing metastatic prostate cancer cells comprises administering to the man a therapeutically effective amount of a drug complex which comprises three components: a targeting carrier molecule which is selectively delivered to prostate tissue, bone or both; a linker which comprises a component acted upon by prostate specific antigen (PSA) which is present in the microenvironment of malignant prostatic epithelial cells; and a cytotoxic drug which is toxic to prostatic cancer cells. The present invention also relates to a method of treating metastatic cancer in an individual, in which the drug complex described above is administered to a man with prostate cancer, in a quantity sufficient to deliver the cytotoxic drug to prostate cancer cells at a concentration sufficient to kill some or all of the cancer cells or inhibit replication or division of the cancer cells. Drug complexes useful in the method of treating prostate cancer and the method of killing prostate cancer cells (such as androgen independent cells) are also the subject of this invention.

In a further embodiment, the drug complex comprises a targeting carrier molecule which is an imaging agent for prostate and prostate derived tumors, such as fluoropropylputrescine (e.g., N-3 fluoropropylputrescine); a peptide which serves as a linker and comprises amino acid residues acted upon by PSA; and a cytotoxic drug, which is linked to the targeting carrier molecule by the peptide. The linker can be comprised of more than one type of molecule, as described herein. The drug complex is administered to an individual by any route which results in delivery of the cytotoxic drug to prostate cells. In one embodiment, the drug complex is administered intravenously.

Combining a targeting carrier molecule with specificity for prostate tissue, bone or both with a cytotoxic drug, which are joined by a linking peptide that is a substrate for PSA, provides a treatment for cancer having higher efficacy and lower toxicity than presently available treatments.

BRIEF DESCRIPTION OF THE DRAWINGS

FIG. 7 shows a model compound (4) that demonstrated that pABA is a good leaving group and that pABA can activate the tyrosine carbonyl for hydrolysis. FIG. 7 further shows a compound (5) comprising a succinyl ester group (MeO-Suc) attached to a tripeptide (Arg-Pro-Tyr), which is attached to pABA, which is attached to adriamycin. Finally, FIG. 7 shows a compound (6), which arises as a result of the cleavage of compound (5) by PSA.

FIG. 8 shows a compound (7) comprising a succinyl ester group (MeO-Suc) attached to a tripeptide (Arg-Pro-Tyr), which is attached to pABOC, which is attached to adriamycin. FIG. 8 further shows how the fluorine-containing pABOC, being electron-withdrawing, activates the tyrosine carbonyl toward hydrolysis (8). Finally, FIG. 8 shows how the spontaneous breakdown of 8, results in the release of "native" adriamycin.

DETAILED DESCRIPTION OF THE INVENTION

The present invention relates to a method of selectively delivering a drug or other agent to a particular cell type by means of a drug complex which includes at least three components: a targeting carrier molecule which is selectively distributed to the cell type or tissue to which the drug or agent is to be delivered; a linker which is acted upon (cleaved or otherwise broken or disrupted) by a molecule present at the site to which the drug or agent is to be delivered; and a drug or agent to be delivered. The invention also relates to the drug complex, which, optionally, includes additional components. In the method, the drug complex is administered via an appropriate route to an individual in need of the drug or agent. The drug complex moves to the cells or tissues to which the targeting carrier molecule is specifically delivered. The linker is cleaved by the molecule present at the site to which the drug or agent is to be delivered and the drug or agent is made available to enter into or otherwise interact with the specific cell type. The location(s) in the body at which the tissue or cell type(s) to which a drug or agent is to be delivered are referred to as site(s) of the target cell(s).

In a particular embodiment, the invention is a method of treating prostate cancer by killing prostate cancer cells or inhibiting replication or division of prostate cancer cells, such as androgen independent prostate cancer cells. In this embodiment, the drug complex comprises three components: a targeting carrier molecule which is any agent or molecule which is selectively delivered to prostate, bone or both; a linker which is cleaved by PSA; and a drug which is cytotoxic to cancer cells, particularly androgen independent prostatic cancer cells. Additionally, the linker may be comprised of more than one type of molecule. For example, the linker may comprise a substrate for a molecule as described previously, and may also include one or more other molecules, such as one or more desirable chemical molecules, e.g. para-amino benzoic acid (pABA) and para-aminobenzyloxycarbonyl (pABOC).

A selectively delivered drug is one which is delivered or distributed to the targeted cell or tissue to an extent sufficient for delivery of the drug or agent, such as a cytotoxic drug or agent, in a quantity or concentration sufficient to have the desired therapeutic or diagnostic effects. In the case of treatment of cancer, such as the treatment of prostate cancer, the desired effect is killing of some or all of the cancer cells (e.g., prostatic cancer cells) in an individual or at least a reduction in replication or division of the cancerous cells. In other words, the targeting carrier molecule generally will be a molecule which is distributed to a limited number of sites within the body, but it is not necessary that it be delivered only to those sites. For example, the targeting carrier molecule can be an imaging agent, such as N-3 fluoropropy-lputrescine which is selectively distributed to prostate and bone, relative to blood and muscle, after administration to a man. In the embodiment in which prostate cancer is treated, the targeting carrier molecule is a polyamine (e.g., putrescine, spermine or spermidine) because of its affinity to prostatic cancer cells through the polyamine surface receptor molecules present on prostatic epithelial cells.

The linker, which is acted upon by a molecule which is present at an effective concentration in the environs of the specific cell, may be any entity which is acted upon by a molecule, such as an enzyme, at or within a given target cell. Acted upon is defined as any change in the linker induced by the molecule at or within the given target cell which results in release of the drug.

In the embodiment in which the drug complex is used to treat prostate cancer, the linker comprises amino acid residues which are acted upon by PSA. The linker used comprises at least those amino acid residues necessary for PSA to act, resulting in cleavage of the linker and release of the cytotoxic drug. The linker may comprise additional amino acid residues, which may be the same as those in the PSA peptide substrate or different (e.g., they can be random or filler amino acid residues, amino acid residues which enhance uptake of the cytotoxic drug into the prostatic cancer cell, amino acid residues which stabilize the cytotoxic drug or enhance its resistance to degradation once inside the cell or amino acid residues which are substrates for cellular enzymes). Optionally, the linker can comprise more than one type of molecule. For example, the linker may comprise amino acid residues acted upon by PSA as described previously, and may also include one or more other molecules, such as one or more desirable chemical molecules, e.g. para-amino benzoic acid (pABA) and para-aminobenzyloxycarbonyl (pABOC).

Examples of possible amino acids that can be used in the subject invention include the following combinations of amino acid residues, as represented in Table 1 of Denmeade et al., Cancer Research 57: 4924–4930 (1997): KGISSQY (SEQ ID NO.: 1); SRKSQQY (SEQ ID NO.: 2); GQKGQHY (SEQ ID NO.: 3); EHSSKLQ (SEQ ID NO.: 4); QNKISYQ (SEQ ID NO.: 5); ENKISYQ (SEQ ID NO.: 6); ATKSKQH (SEQ ID NO.: 7); KGLSSQC (SEQ ID NO.: 8); LGGSQQL (SEQ ID NO.: 9); QNKGHYQ (SEQ ID NO.: 10); TEERQLH (SEQ ID NO.: 11); GSFSIQH (SEQ ID NO.: 12); HSSKLQ (SEQ ID NO.: 13); SKLQ (SEQ ID NO.: 14); KLQ (SEQ ID NO.: 15) and LQ (SEQ ID NO.: 16).

Another example of a possible combination of amino acids that can be used in the subject invention is AKFE (SEQ ID NO.: 17).

In the bloodstream, the peptide link between the targeting carrier molecule and the cytotoxic drug will be sustained because there is insufficient unbound PSA to act to a significant extent on the linking peptide that is substrate for unbound PSA. In the microenvironment of the androgen independent prostate cancer cells, where unbound PSA is found in large concentrations, PSA will cleave the linking peptide to a great extent and thereby release the cytotoxic drug into the cell. By having the features of specificity for prostate and bone and the required presence of unbound PSA for drug release, the targeting carrier molecule is highly target specific for the androgen independent prostate cancer cell. Such a highly target specific targeting carrier molecule will increase the efficacy of and decrease the toxicity of the cytotoxic drug component used. Targeting molecules can be, for example, polyamines, e.g., putrescine, spermine or spermidine, which provide affinity to prostatic cancer cells through the polyamine surface receptor molecules present on prostatic epithelial cells. A specific example of such a targeting carrier molecule is N-3 fluoropropylputrescine. (Hwang, D. et al., J. Nucl. Med., 30:1205–1210 (1989)).

The cytotoxic drug which is a component of the drug complex can be any agent effective in killing prostate cancer cells, including metastatic prostate cancer cells. For example, any of the following drugs can be used: adriamycin, amonafide, cisplatin, carboplatin (CBDCA), CHIP, cyclophosphamide, doxorubicin, epirubicin, estramustine, etoposide, 5-fluorouracil, gallium nitrate, idarubicin, ifosfamide+mesna, ketoconazole, liarozole (R85,246), methotrexate, mitomycin C, mitoguazone, mitoxantrone, proscar (finasteride), suramin, taxol, thapsigargin, trimetrexate, vinblastine (CI), and vinblastine and emcyt.

Adriamycin is particularly desirable for several reasons. First, it gives a response rate of 15–20% in hormone refractory metastatic prostate cancer with a median survival of 33 weeks. These results are among the best noted for single agents in this disease. (Kreis, W., Cancer Investigation, 13:296–312 (1996)). Second, the chemistry is well established. For example, adriamycin can be easily coupled to peptides through its amino (—NH$_2$) group. (Nogusa, H. et al., Chem. Pharm. Bull. Jpn., 43:1931–1936 (1995). Moreover, several of its analogs, including N-substituted ones, are known to display high anticancer activity. (Israel, A. et al., Cancer Treatment Reviews, 14:163–167 (1987).

Another cytotoxic drug, Thapsigargin, is a sesquiterpene lactone extracted from the roots of the umbelliferous plant Thapsia garganica L. (Thastrup, O. et al., Proc. Nat. Acad. Sci., USA, 87:2466–2470 (1990)). This highly lipophilic agent specifically inhibits Ca$^{++}$-ATPase pumps of the endoplasmic reticulum, but not the pumps of erythrocytes, plasma, or mitochondrial membranes.

In vitro treatment with 500 nm thapsigargin in a series of both rat and human androgen independent prostate cancer cell lines, which either express or completely lack p53 protein expression, results in the elevation of intracellular Ca$^{++}$. Within 72 to 96 hours, these cells undergo apoptosis and lose their clonogenic potential.

The dose of the drug complex to be used is a sufficient quantity of complex to result in delivery and availability to target cells of the cytotoxic drug at a therapeutically effective level. Dose will be determined empirically and will be determined, for example, by the stage or condition of the disease for which an individual is being treated, the individual's general health, size, age, and sex. In the embodiment of the present invention in which a man is treated for prostate cancer, the dose will be determined by taking into consideration the cytotoxic drug being used, the stage of the cancer, and the man's age, general health and size.

The timing and number of doses of the drug complex administered will also be determined empirically. The number of doses may be at any interval sufficient to promote or to result in killing of cells and/or inhibition of replication or division. For example, the drug complex can be administered hourly, daily, weekly, monthly, or any combination thereof.

The route of administration can be any route that delivers a therapeutically effective quantity of the drug complex to the target cells, such as to prostate cancer cells. The formulation of the drug complex can be any pharmaceutically effective formulation or carrier, such as any physiologically acceptable buffer, saline solution, or water.

In one embodiment, the prodrug of the invention has the structure shown below, and is believed to have a prostate specific antigen (PSA) cleavage site as indicated.

PSA Cleavage Site

Where R represents a polyamine attached through the amino group of the N-terminal amino acid Histidine, and Adriamycin, indicates attachment of Adriamycin (structure given below) through its amino group.

One method of forming this prodrug is shown below:

The present invention is illustrated by the following examples, which are not intended to be limiting in any way.

EXAMPLE 1

In Vitro Testing of Drug Complexes

PC3 and DU-145 androgen-independent human prostate cancer cell lines obtained from the American Tissue Culture Collection (ATCC) are used for in vitro studies. Cells are grown as monolayer cultures in RPMI 1640 medium supplemented with 10% fetal bovine serum, 2 mM glutamine and antibiotics. Radiation survival curves and radiation-induced apoptotic DNA fragmentation patterns in these cell lines are already established in the laboratory. Cells are treated with this drug, carrier-peptide, or carrier-peptide-drug complex with or without radiation. After 24 hours, the cells are trypsinized and plated for clonogenic survival studies. Apoptotic response to the treatments is determined by: 1) agarose gel electrophoresis analysis of DNA fragmentation at 48 and 72 hours after treatment, 2) morphological observations after staining with DAPI, and 3) terminal deoxytransferase-mediated dUTP Nick End Labeling (TUNEL) assay.

EXAMPLE 2
In Vivo Testing of Drug Complexes

Two human prostate carcinoma tumor lines grown as xenografts in male SCID mice are used: the human DU-145 prostate carcinoma which is not androgen dependent and the human LNCaP prostate carcinoma which produces PSA and has a well characterized androgen receptor and response to androgens. The drug complexes are administered up to maximally tolerated doses alone and in conjunction with fractionated radiation therapy ($^{137}$Cs Gamma Cell 40) delivered to the tumor bearing limb.

The progress of each tumor is assessed thrice weekly by caliper measurements until the tumors reach 2000 mm$^3$. Tumor growth delay is calculated as the number of days for each tumor to reach a volume of 500 mm$^3$ as compared to untreated controls. The efficacy of combination treatments is assessed using isobologram analysis for determination of additivity/synergy.

PHASE I CLINICAL TRIAL: (MAXIMAL TOLERABLE DOSE ASSESSMENT)

Based on the results of the in vitro and in vivo studies of the drug complexes, a drug complex is chosen for testing in ten patients with hormone refractory metastatic prostate cancer. A single intravenous dose of the drug complex is given on an inpatient basis with cardiorespiratory monitoring. Toxicity evaluation of all major organ systems is evaluated using blood, urine, stool, and, if necessary, bone marrow studies. Doses are escalated in 10% increments per patient until the maximal response with acceptable toxicity is reached. Response is assessed using a combination of a weekly digital rectal examination (DRE), PSA, LDH, hemoglobin, and monthly bone scan. The starting dose is selected based on the toxicity data from the preceding animal studies.

EXAMPLE 3
Effect of Thapsigargin (TG) on Cell Proliferation in vitro

Preliminary in vitro data indicate that TG inhibits cell proliferation (Table 1, DU 145 cells) and clonogenic cell survival (Table 2, PC3 cells) of androgen independent human prostate cancer cells.

Table 1 shows the effect of thapsigargin and radiotherapy on proliferation of DU-145 prostate cancer cells. The results indicate that thapsigargin inhibits cell proliferation in vitro.

TABLE 1

Effect of TG and RT on proliferation of DU-145 prostate cancer cells*

| Thapsogargin (nM) | Total Number of Cells per Dish (10$^6$) | | | |
| --- | --- | --- | --- | --- |
| | 0 Gy | 2 Gy | 4 Gy | 8 Gy |
| 0 | 2.1 | 1.4 | 1.2 | 0.5 |
| 20 | 1.0 | 0.8 | 0.3 | 0.4 |
| 100 | 0.7 | 0.5 | 0.5 | 0.4 |
| 400 | 0.7 | 0.4 | 0.3 | 0.3 |

*Cells were irradiated 2 hours after adding TG or DMSO. At 48 hours cells were trypsinized and counted after staining with trypan blue. <5% of the cells were trypan blue + at that time.

Table 2 shows the effect of thapsigargin and radiotherapy on clonogenic cell survival of PC3 prostate cancer cells. The results indicate that thapsigargin inhibits clonogenic cell survival in vitro.

TABLE 2

Effect of TG and RT on clonogenic survival of PC3 cells**

| Thapsigargin (nM) | Surviving Fraction (SF) (PE treated/PE control) | | | NET survival (SF/TG toxicity) | |
| --- | --- | --- | --- | --- | --- |
| | 0 Gy | 2 Gy | 4 Gy | 2 Gy | 4 Gy |
| 0 | 1 (0.8) | 0.57 | 0.38 | 0.57 | 0.38 |
| 20 | 0.69 | 0.42 | 0.23 | 0.61 | 0.33 |
| 50 | 0.80 | 0.39 | 0.23 | 0.49 | 0.29 |
| 100 | 0.62 | 0.25 | 0.18 | 0.40 | 0.30 |
| 200 | 0.58 | 0.25 | 0.13 | 0.43 | 0.22 |
| 400 | 0.60 | 0.25 | 0.13 | 0.42 | 0.22 |

PE (Plating Efficiency)
**Cells were irradiated 2 hours after adding TG or DMSO. At 24 hours cells were trypsinized and plated for clonogenic assay in a drug free media. Colonies were stained with 0.4% crystal violet on the 12th day and viable colonies of >50 cells were counted.

EXAMPLE 4
Effect of Thapsigargin (TG) on Cell Proliferation in vivo

Figure 1:
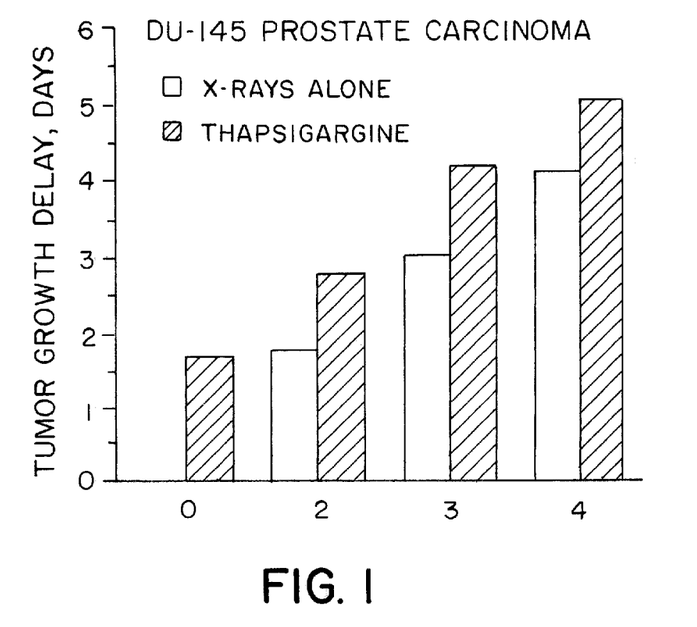
FIG. 1 is a graphic representation of growth delay of the human DU-145 prostate carcinoma xenograft after treatment with fractionated radiation therapy (RT) on days 7–11 or with thapsigargin (TG) on days 4–18.
Figure 2:
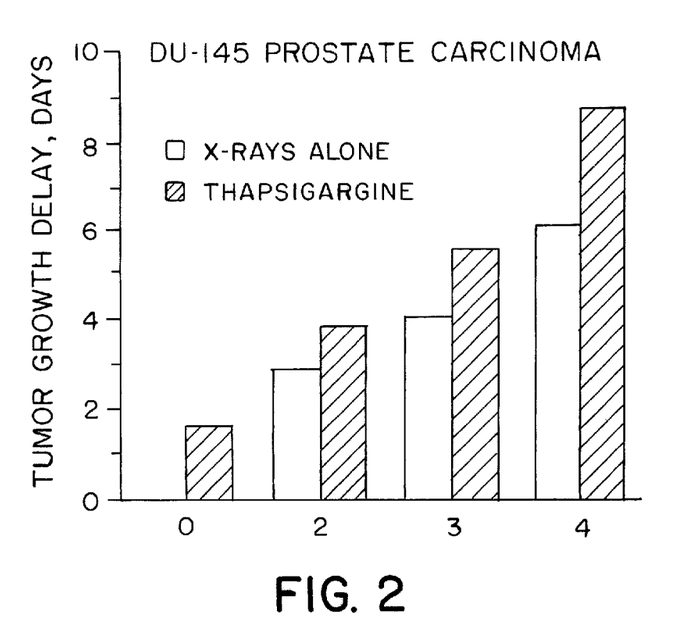
FIG. 2 is a graphic representation of growth delay of the human DU-145 prostate carcinoma xenograft after treatment with fractionated RT on days 7–11 and 14–18 or with TG on days 4–18.
Figure 3:
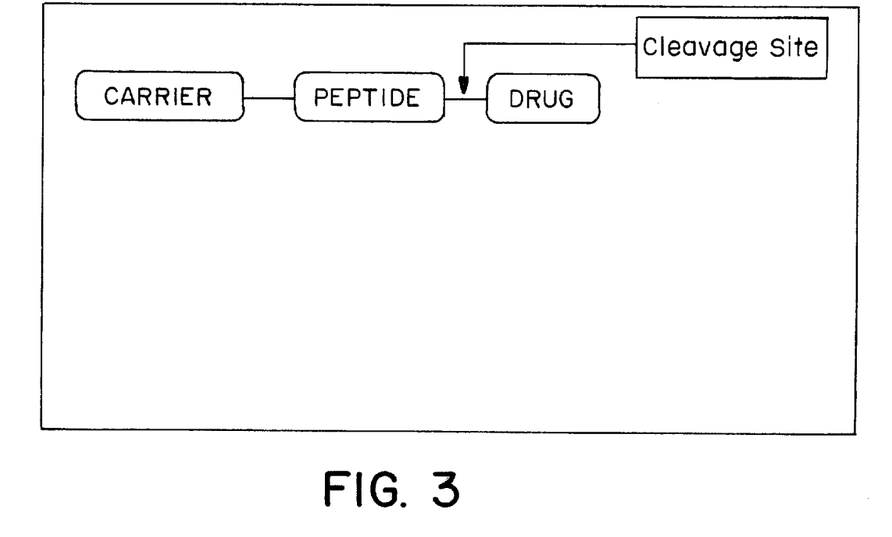
FIG. 3 is a schematic representation of one embodiment of a drug complex of the present invention, which comprises a targeting carrier molecule ("carrier"), a peptide linker ("peptide"), and a drug ("drug"); the peptide is a substrate for a molecule whose action at the cleavage site results in cleavage of the drug from the drug complex.
Figure 4:
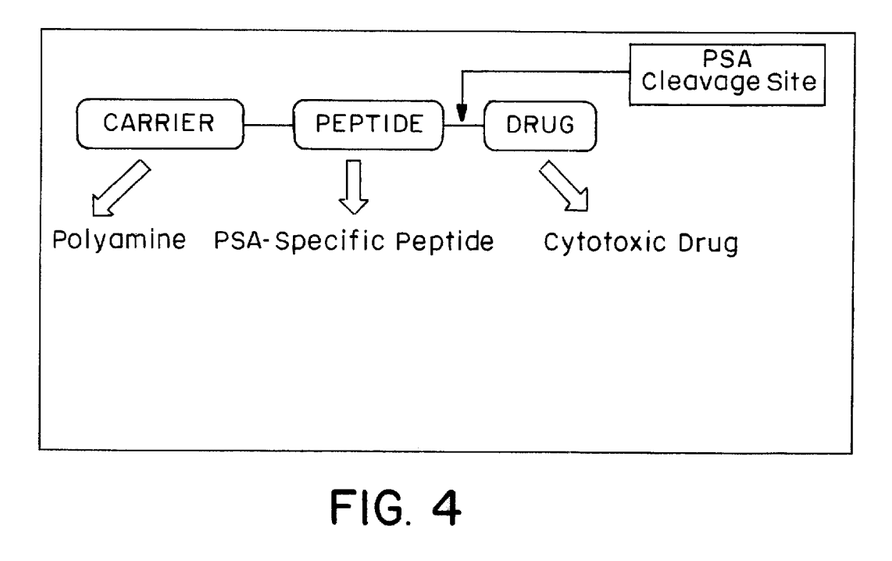
FIG. 4 is a schematic representation of one embodiment of a drug complex of the present invention in which the carrier is a polyamine, the peptide is a PSA-specific peptide and the drug is a cytotoxic drug.

Male SCID mice bearing the human DU-145 prostate carcinoma Xenograft growing subcutaneously in a hindlimb were treated daily with TG (0.5 mg/kg) by IP injection from day 4–18 post tumor cell implantation. Some animal groups also received fractionated RT locally to the tumor bearing region on days 7–11 or days 7–11 and 14–18. FIG. 1, low dose TG (0.5 mg/kg) administration produced a measurable tumor growth delay and, when given in conjunction with RT, the independent effects of TG and RT were additive. Moreover, when the RT regimen was extended to 2 weeks, the additional benefit of the TG administration was maintained.

EXAMPLE 5
PSA Cleaving of pNA Derivative

Figure 5:
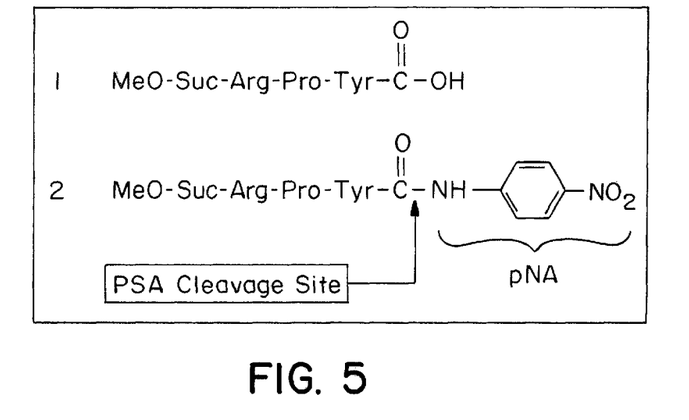
FIG. 5 is a schematic representation of a tyrosine-containing tripeptide (1) to which a succinyl ester group (MeO-Suc) is attached and of a para-nitroanilide (pNA) derivative of the tyrosine-containing peptide (2), with the PSA cleavage site indicated by an arrow.

A tyrosine tripeptide (compound 1 in FIG. 5) was prepared using methods known to those in the peptide chemistry art. It is known that PSA cleaves its para-nitroanilide (pNA) derivative at the tyrosine site (compound 2 in FIG. 5). (Christensson, A. et al., Eur. J Biochem., 194:755–763 (1990)). It is also known that the "released" pNA makes it possible to study this reaction colormetrically. Using this feature, it was demonstrated that the sonicate from a cell line that is known to produce PSA, i.e. LNCaP, cleaves compound 2 in FIG. 5. It was also shown that a negative control, i.e. CV-1 cell line, that does not produce PSA did not cleave compound 2 in FIG. 5 and that neither newborn calf serum, nor pooled human serum cleaved compound 2 in FIG. 5. These results indicate that a "PSA-like" activity exists in the sonicate of LNCaP (and not in human or fetal calf serum) that can cleave compound 1 in FIG. 5 at the tyrosine site and release pNA.

Figure 6:
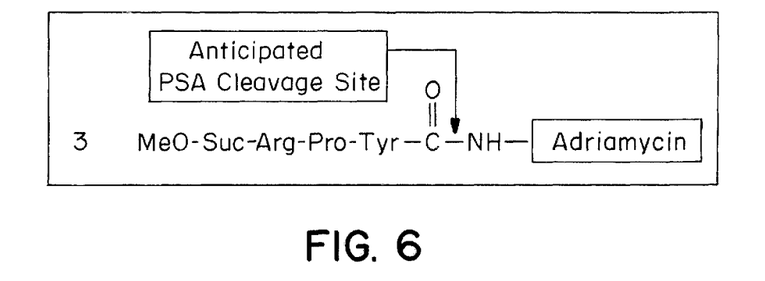
FIG. 6 is a schematic representation of a tyrosine-containing tripeptide with adriamycin attached directly to the tripeptide via adriamycin's $NH_2$ group; MeO-Suc represents a succinyl ester group attached to the tyrosine-containing tripeptide.

Based on the above results, the pNA group was replaced with adriamycin, i.e. by attaching adriamycin directly to the tyrosine (FIG. 6) via adriamycin's —$NH_2$ group. It was hypothesized that PSA would cleave the molecule of FIG. 6 at the tyrosine site and release adriamycin. However, there was no cleavage and no release of adriamycin.

There are several reasons why cleavage and release did not occur. First, pNA, because of its electron withdrawing para-$NO_2$ group, is a better leaving group than adriamycin. Second, because pNA is electron-withdrawing, it can greatly activate the tyrosine carbonyl group toward hydrolysis relative to adriamycin. Finally, since adriamycin is sterically bulkier than the pNA group, the drug may have prevented PSA from approaching the tyrosine site.

EXAMPLE 6

Construction of Molecules Containing para-Amino Benzoic Acid and para-Aminobenzyloxycarbonyl Attaching adriamycin to a tripeptide molecule (see compound 1 of FIG. 5) through a para-amino benzoic acid can solve the problems previously discussed for the following reasons (a) pABA can function as a good leaving group because it contains an electron withdrawing carbonyl group in the para-position, (b) because pABA is electron-withdrawing, it can activate the tyrosine carbonyl hydrolysis, and (c) PSA activity may not be sterically hindered as the pABA linker can keep adriamycin away from the tyrosine cleavage site.

The results with this molecule indicate that pABA is a good leaving group and that it can activate the tyrosine carbonyl for hydrolysis. That is, the sonicate of LNCaP that showed "PSA-like" activity cleaved compound 4 of FIG. 7 at the tyrosine site and released pABA.

Figure 7:
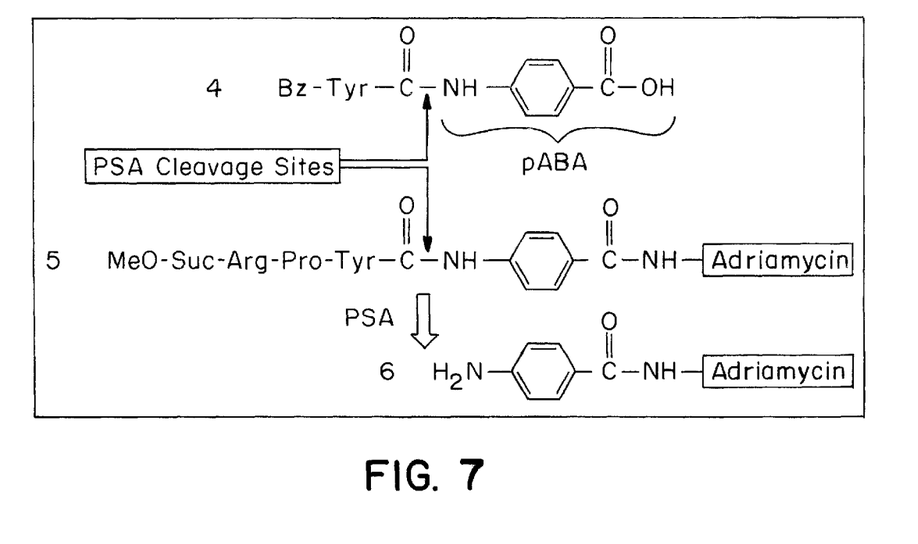
FIG. 7 is a schematic representation of one embodiment of the present invention in which the synthesized compound contains pABA.

Since it is established, based on the above results, that there is a linker suitable for the attachment of adriamycin, compound 5 of FIG. 7 can be synthesized. Furthermore, it can be examined to determine if it can also be cleaved at the tyrosine site to release an active form of adriamycin, namely compound 6 of FIG. 7.

Cleavage of compound 5 can be assessed using the sonicate of LNCaP that exhibits "PSA-like" activity. It is expected that cleavage will occur at the tyrosine site of compound 5. However, what will be "released" is an analog of adriamycin (compound 6 of FIG. 7) and not adriamycin itself. The ability of this analog to intercalate DNA can be assessed and compared with that of native adriamycin using known methods, such as measurement of emissions at 450 nm on ethanol-precipitated DNA. The data is also normalized for efficiency of precipitation by assaying the DNA at 260 nm.

Figure 8:
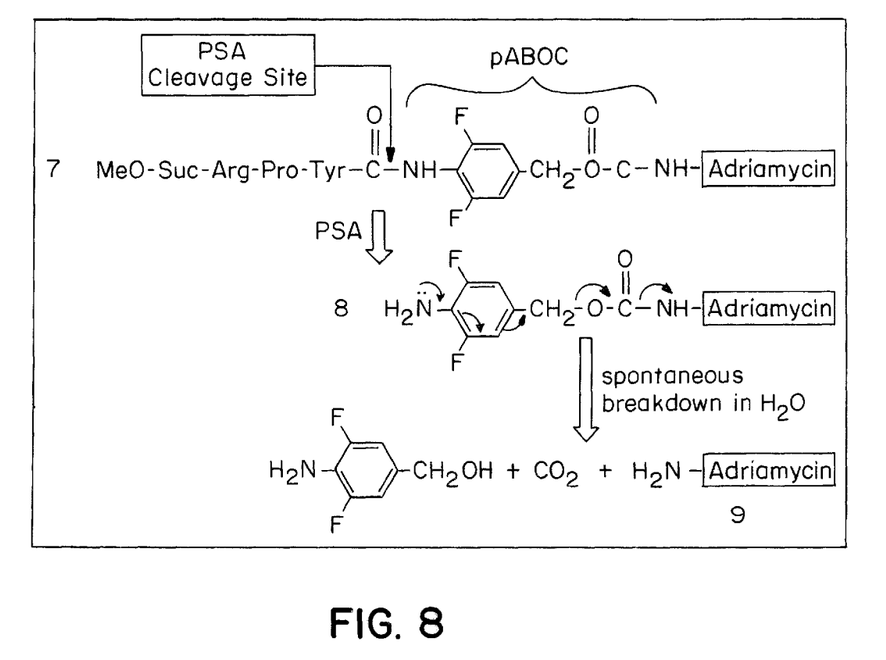
FIG. 8 is a schematic representation of one embodiment of the present invention in which the synthesized compound contains pABOC.

An alternative approach takes advantage of a compound that is similar to pABA. This compound is para-aminobenzyloxycarbonyl (pABOC), which offers the advantage of breaking down spontaneously (compound 8 of FIG. 8) to release "native" adriamycin (i.e. adriamycin lacking N-substituents; compound 9 of FIG. 8). Because of the similarity between pABA and pABOC, the latter offers many of the same advantages. First, since the physical size of pABOC is similar to that of pABA, it can keep the "bulky" adriamycin away from the tyrosine cleavage site. Second, electron-withdrawing fluorine substituents to be added at the two ortho-positions (shown in compounds 7 and 8 of FIG. 8) should make pABOC a good leaving group without introducing any steric bulk, since fluorine and hydrogen atoms are essentially the same size. Finally, the fluorine-containing pABOC is electron-withdrawing and, thus, can also activate the tyrosine carbonyl toward hydrolysis. Based on this information, it can be expected that PSA will cleave compound 7 of FIG. 8 at the tyrosine site and release compound 8 of FIG. 8. Then, as described above, compound 8 of FIG. 8 should break down spontaneously under physiological conditions to release "native" adriamycin. This can be assessed using known methods.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of delivering a drug or a diagnostic agent to prostate cancer cells in an individual comprising administering to the individual a drug complex which comprises:

a) a polyamine targeting carrier molecule which is selectively distributed to prostate cells;

b) a drug or an agent to be delivered to the prostate cells; and c) a linker connecting the polyamine and the drug or agent, said linker comprising a peptide having a prostate specific antigen cleavage site, wherein the drug complex is administered by a route which permits delivery of the drug complex to the prostate cancer cells.

2. The method of claim 1, wherein the polyamine is selected from the group consisting of putrescine, spermine, and spermidine.

3. The method of claim 2, wherein the putrescine is fluoropropylputrescine.

4. The method of claim 1, wherein the peptide linker additionally comprises a good leaving group connecting the prostate specific antigen cleavage site and the drug or agent.

5. The method of claim 4, wherein the drug complex is administered intravenously.

6. The method of claim 5, wherein the drug or agent is selected from the group consisting of: adriamycin, amonafide, cisplatin, carboplatin (CBDCA), CHIP, cyclophosphamide, doxorubicin, epirubicin, estramustine, etoposide, 5-fluorouracil, gallium nitrate, idarubicin, ifosfamide+mesna, ketoconazole, liarozole (R85,246), methotrexate, mitomycin C, mitoguazone, mitoxantrone, proscar (finasteride), suramin, taxol, thapsigargin, trimetrexate, vinblastine (CI), and vinblastine and emcyt.

7. The method of claim 4, wherein the good leaving group is:

or wherein the amine group of the good leaving group is bound to the prostate specific antigen cleavage site and the carbonyl group is bound to the drug or agent.

8. The method of claim 7, wherein the drug complex is:

or

9. The method of claim 1, wherein the peptide linker is selected form SEQ ID NOS 1–17.

* * * * *

UNITED STATES PATENT AND TRADEMARK OFFICE
CERTIFICATE OF CORRECTION

PATENT NO.    : 6,368,598 B1                                              Page 1 of 1
DATED         : April 9, 2002
INVENTOR(S)   : Anthony V. D'Amico, Glenn J. Bubley, David J. Jebaratnam and
                James S. Weinberg It is certified that error appears in the above-identified patent and that said Letters Patent is hereby corrected as shown below:

<u>Title page,</u>
Item [73], Assignees, should read as follows:

-- JCRT Radiation Oncology Support Services, Inc., Boston, Massachusetts, Northeastern University, Boston Massachusetts and Beth Israel Deaconess Medical Center, Boston, Massachusetts. --

Signed and Sealed this

Twenty-second Day of October, 2002

Attest:

JAMES E. ROGAN
*Attesting Officer*        *Director of the United States Patent and Trademark Office*

SEQUENCE LISTING

```
<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Lys Gly Ile Ser Ser Gln Tyr
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2
```

Ser Arg Lys Ser Gln Gln Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Gly Gln Lys Gly Gln His Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Glu His Ser Ser Lys Leu Gln
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gln Asn Lys Ile Ser Tyr Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Glu Asn Lys Ile Ser Tyr Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Ala Thr Lys Ser Lys Gln His
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

```
Lys Gly Leu Ser Ser Gln Cys
 1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Leu Gly Gly Ser Gln Gln Leu
 1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gln Asn Lys Gly His Tyr Gln
 1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Thr Glu Glu Arg Gln Leu His
 1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gly Ser Phe Ser Ile Gln His
 1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

His Ser Ser Lys Leu Gln
 1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

Ser Lys Leu Gln
```

-continued

```
<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

Lys Leu Gln
  1

<210> SEQ ID NO 16
<211> LENGTH: 2
<212> TYPE: PRT
<213> ORGANISM: Artificial Sequence
<220> FEATURE:
<223> OTHER INFORMATION: Synthetic

<400> SEQUENCE: 16

Leu Gln
  1

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Ala Lys Phe Glu
```